US00PP28078P3

(12) United States Plant Patent
Byrne et al.

(10) Patent No.: US PP28,078 P3
(45) Date of Patent: Jun. 6, 2017

(54) NECTARINE TREE NAMED 'SMOOTH TEXAN THREE'

(50) Latin Name: *Prunus persica*
Varietal Denomination: Smooth Texan Three

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 113 days.

(21) Appl. No.: 14/544,512

(22) Filed: Jan. 13, 2015

(65) Prior Publication Data

US 2016/0205827 P1 Jul. 14, 2016

(51) Int. Cl.
*A01H 5/08* (2006.01)

(52) U.S. Cl.
USPC ..... Plt./190

(58) Field of Classification Search
USPC ..... Plt./190
See application file for complete search history.

(56) References Cited

U.S. PATENT DOCUMENTS

PP8,948 P 10/1994 Bradford et al.

OTHER PUBLICATIONS

Philips. 2013. AgriLife Today.*
The Brooks and Olmo Register of Fruit and Nut Varieties, 3rd Ed., American Society of Horticultural Science Press, Alexandria, VA, 1997.
Brooks, R. M. 1958. Double Delight, Earligold, and June Gold peaches. Fruit Var. J. 3:22.

* cited by examiner

*Primary Examiner* — Keith Robinson
(74) *Attorney, Agent, or Firm* — Ramey & Schwaller, LLP

(57) ABSTRACT

Disclosed is a new variety of *Prunus persica* named 'SMOOTH TEXAN THREE'. This new variety, which requires approximately 650 chilling units of dormancy, is considered to be a nectarine tree of early mid-season maturity, which ripens in late May to early June in the medium chill zone of Texas and which produces yellow fleshed fruit that are firm, attractively colored, with excellent sub-acid flavor and suitable for both local and regional markets.

4 Drawing Sheets

BACKGROUND OF THE INVENTION

Field of the Invention

This invention relates to nectarine trees and, more specifically, to nectarine trees referred to as a variety of *Prunus persica* named 'SMOOTH TEXAN THREE'. 'SMOOTH TEXAN THREE', which requires approximately 650 chilling units of dormancy, produces high quality, firm clingstone, sub-acid yellow-fleshed nectarines that mature early mid-season.

SUMMARY OF THE INVENTION

The 'SMOOTH TEXAN THREE' (TX4C189LN) nectarine is characterized as to novelty and is otherwise noteworthy by being adapted to the medium chill zone and producing fruit that ripens in the early season. It is considered high quality, is firm and has an attractive coloration. The present variety of nectarine tree bears fruit that are ripe for commercial harvesting and shipment in the late May or early June, when the fruit is grown in the medium chill zone of Texas. 'SMOOTH TEXAN THREE' ripens with the 'June Gold' (not patented, Brooks, 1958) peach. Additionally, the new variety exhibits the potential to be commercialized in regions that have chilling requirements that are relatively low.

Origin of the Variety

The present nectarine tree was the result of an ongoing Stone Fruit Breeding Program of Texas A & M University, College Station, Brazos County, Tex. To this end, controlled crosses are made each year to produce seedling populations from which improved progenies are evaluated and selected.

The seedling TX4C189LN was originated at the Texas A & M University Horticultural Farm in College Station, Tex. in 2001, and was chosen from a population of seedlings that resulted from a cross between the female parent the nectarine, 'Diamond Ray' (U.S. Plant Pat. No. 8,948, Bradford and Bradford, 1994) and male parent 'Danmo' (not patented) which is an early ripening, medium chill, yellow fleshed, sub-acid nectarine used in protected culture from China (Wang, personal communication). 'Diamond Ray' is a hybrid between the nectarine 'Red Diamond' (U.S. Plant Pat. No. 3,165) and an unnamed seedling (Bradford and Bradford, 1994). 'Danmo' is a hybrid between Ruiguang 2 ('Jingyu'×NJN76) (not patented) and Early Red2 (unknown parentage) (not patented). NJN76 (not patented) was a soft, non-melting, orange-yellow fleshed nectarine which was obtained from Dr. Hough of the Fruit Breeding program at Rutgers University (Lirong Wang, personal communication).

'SMOOTH TEXAN THREE' (TX4C189LN) was marked for subsequent observation and noted as having exceptional characteristics. Two-year and older trees of the variety were subsequently evaluated during the 2004 through 2012 fruit growing seasons in both California (Clovis) and Texas (Fairfield, Terrell and College Station).

Asexual Reproduction of the Variety

'SMOOTH TEXAN THREE' was bud grafted onto virus-free Nemaguard ((not patented), Brooks and Olmo 1997) peach rootstock in June 1998 at the nursery site in Oakdale, Calif. The variety was subsequently planted at the experimental orchard in the central portion of the San Joaquin Valley, near Fowler, Fresno County, Calif. and in three sites in Texas (College Station, Fairfield and Terrell). Fruit from the resulting propagation has been evaluated during the period from 2004 to 2012 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographs. The fruit, flowers, and shoots described and photographed were all obtained from five-year old trees.

BOTANICAL DESCRIPTION OF THE VARIETY

Figure 1:
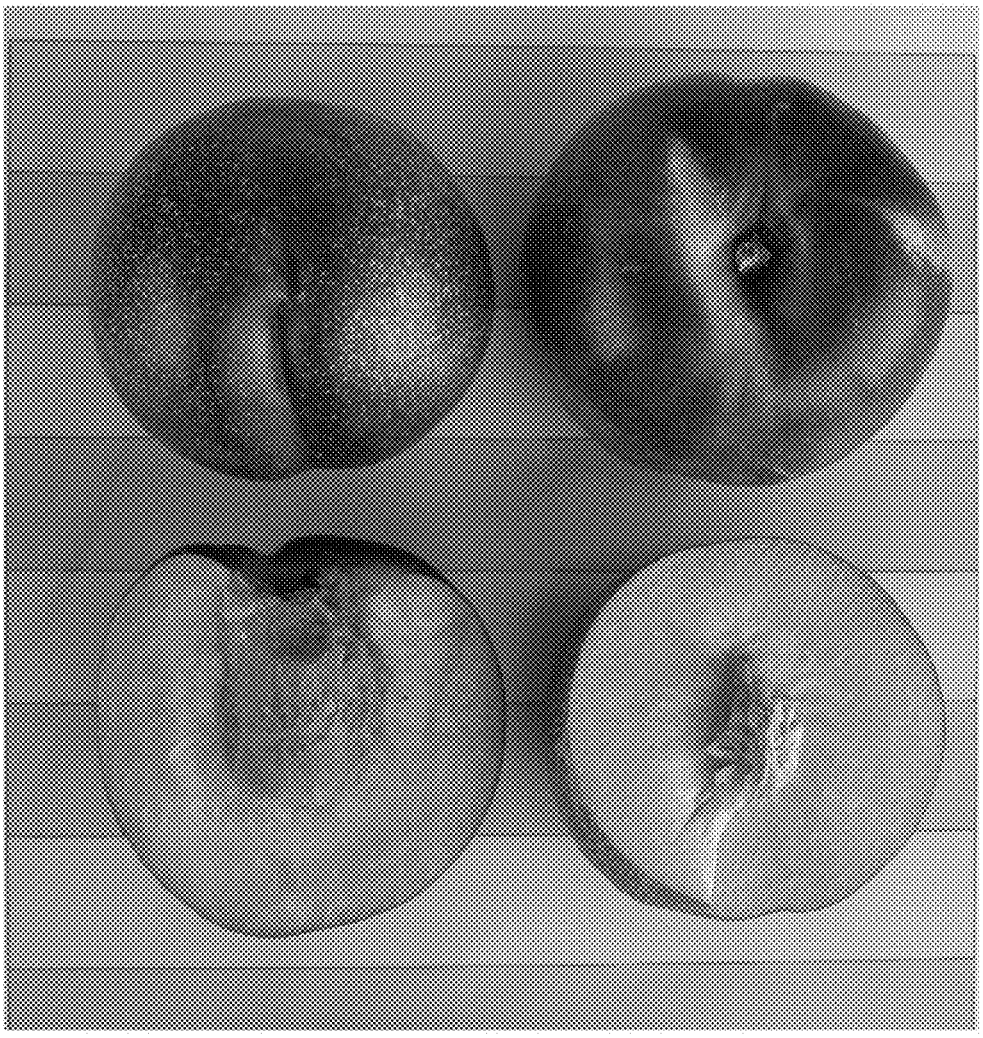
FIG. 1. Color picture showing the flesh and skin color and fruit shape of 'Smooth Texan Three' produced in the evaluation blocks in Clovis, Calif. Thickness of stripes is one inch (2.54 cm).
Figure 2:
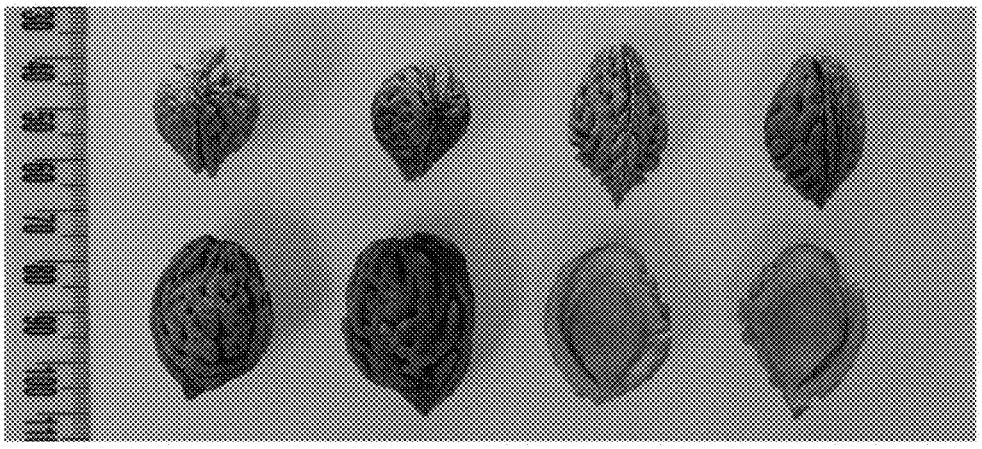
FIG. 2. Color photograph of the endocarp of 'Smooth Texan Three'. The ruler is demarcated in millimeters.
Figure 3:
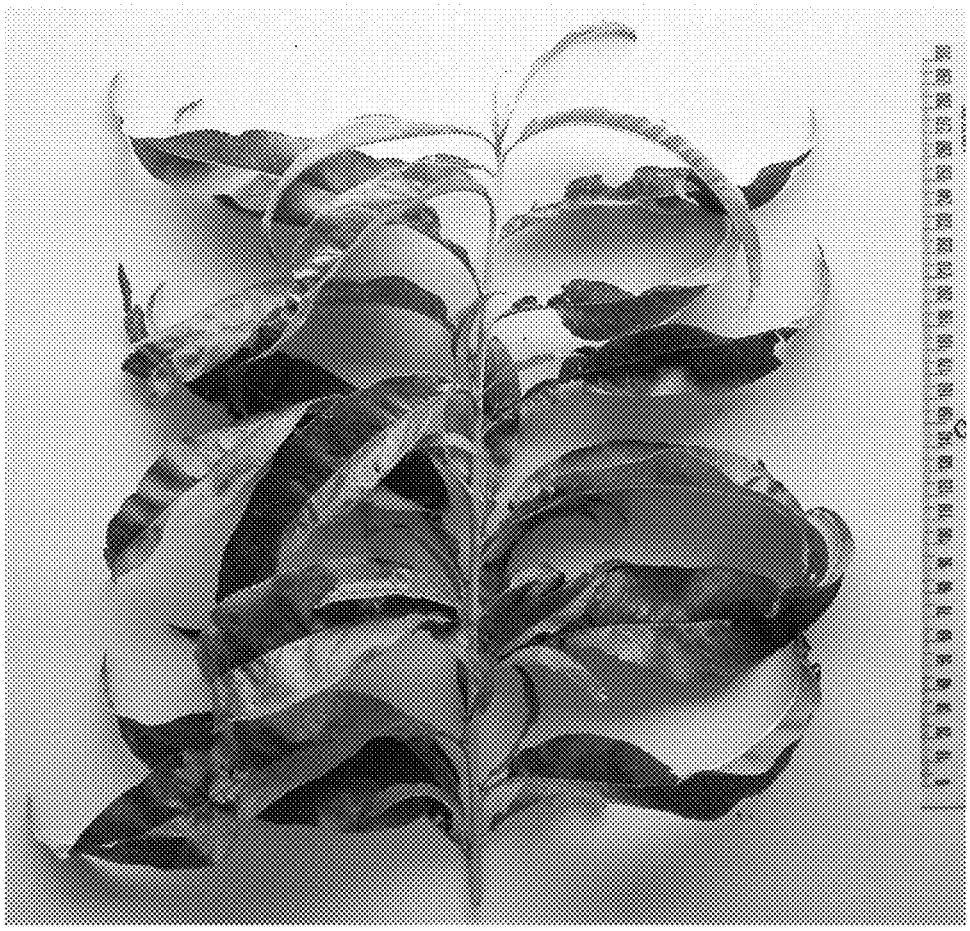
FIG. 3. A stem showing the leaves of the 'Smooth Texan Three' nectarine. The ruler is demarcated in millimeters.
Figure 4:
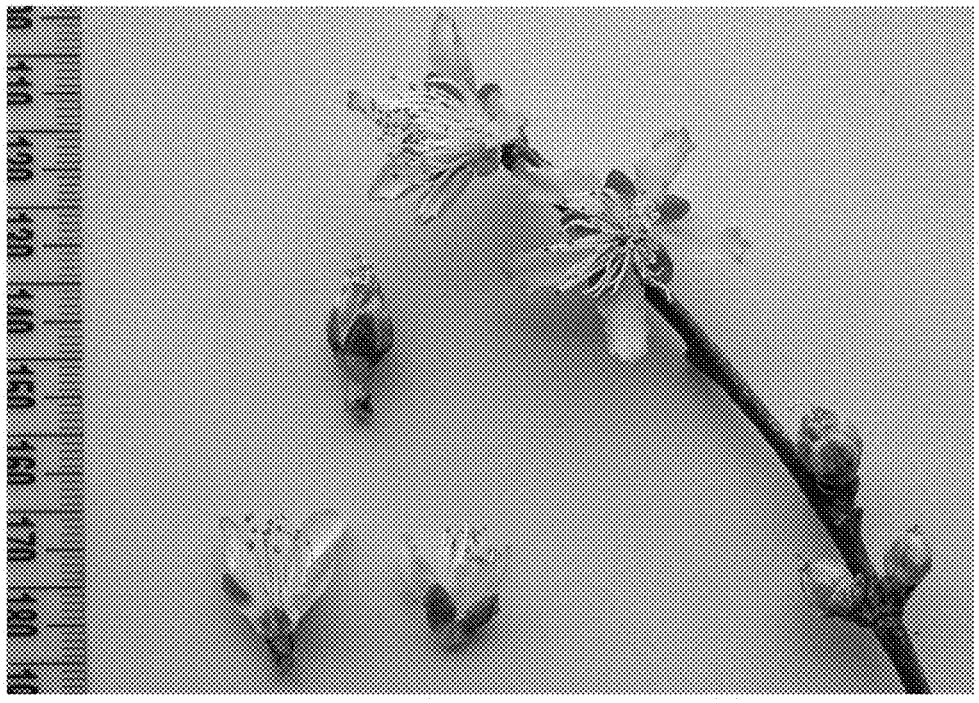
FIG. 4. The non-showy flowers of 'Smooth Texan Three'. The ruler is in millimeters.

Referring more specifically to the pomological details of this new and distinct variety of nectarine tree, the following has been observed under the ecological conditions prevailing at the experimental orchards in College Station and Fairfield, Tex. All major color code designations are by reference to The R.H.S. Colour Chart (2001) provided by The Royal Horticultural Society of Great Britain. Colors are approximate as color depends on horticultural practices such as light level and fertilization rate, among others. The trees used in these descriptions are five-years old.

Tree

Size: Generally average to above average as compared to other common nectarine cultivars ripening in the early mid-season of maturity.

Height: 7 feet (2.13 m) at the end of the 2012 growing season on a five year old tree.

Width: 7 feet (2.13 m) at the end of the 2012 growing season on a five year old tree.

Vigor: High.

Density: Medium to high.

Productivity: Productive.

Shape: The trees are vigorous with the typical semi-spreading growth habit similar to 'TexKing' (U.S. Plant Pat. No. 14,627, 'TexPrince' U.S. Plant Pat. No. 14,629, and 'TexRoyal' (not patented), Byrne and Bacon, 1991).

Current season growth: The current season growth for the new variety was approximately 4.0 to 4.1 feet (1.22-1.25 m).

Regularity of bearing: Regular, and considered hardy under typical central San Joaquin Valley, Calif. environmental conditions.

Trunk

Size: Approximately 4.3 inches (10.8 cm) in diameter and 14.0 inches (35.6 cm) in circumference when measured at a distance of approximately 12 inches (30.5 cm) above the soil level, at the end of the 2012 growing season on a five-year old tree.

Bark texture: Considered moderately rough with numerous folds of papery scarf-like skin being present.

Bark coloration: Variable, colors present are 166A of the Greyed-Orange Group, N200D of the Brown Group and 201D of the Grey Group.

Branches

Size: Considered medium to large for the variety.

Thickness: Average (about 4.6 cm in diameter as measured 10 cm from the trunk on a five-year old tree) as compared to other varieties. The length of the branches is limited by pruning to a 3 to 5 foot (approximately 0.9 to 1.5 m) length depending on the position on the tree.

Surface texture: Average and appearing furrowed on wood that is several years old.

Lenticels: Numerous flat, oval lenticels present. The lenticels range in size from approximately 2 to 5 mm in width and were approximately 1 mm in height.

Current season shoots: Surface texture—Substantially glabrous.

Internode length: Approximately 3.5 to 4.0 cm as measured in the middle of a current season stem.

Color of mature branches: The predominant colors are 165A and 174A-B of the Greyed-Orange Groups, N199C of the Grey-Brown Group and 200D of the Brown Group.

Current season shoots: Color—Medium green (144A-B, N144A&D, 145A and 146D of the Yellow-Green Groups) with some reddish-brown coloration appearing on exposed surface of the shoots (165A and 166D of the Greyed-Orange Groups). The upper exposed surface of the current season growth exhibits weak to medium intensity of anthocyanins.

Leaves

Size: Considered moderately large for the species. Leaf measurements have been taken from vigorous upright current season growth approximately at mid-shoot.

Leaf length: Approximately 159 to 185 mm.

Leaf width: Approximately 43 to 45 mm.

Leaf thickness: Less than 1 mm.

Leaf form: Lanceolate.

Leaf tip form: Acuminate.

Leaf upper surface color: Green varying among 137A-C of the Green Group and 146A-B of the Yellow-Green Group.

Leaf lower surface color: Green varying among 146A-B of the Yellow-Green Group.

Leaf mid-vein color: Light green, similar to 145A-B of the Yellow-Green Group.

Leaf margins:
*Form*.—Considered crenate/crenulate.
*Uniformity*.—Considered generally uniform.
Leaf petioles:
*Size*.—Considered medium long.
*Length*.—Approximately 11 to 13 mm.
*Thickness*.—Approximately 2 mm.
*Color*.—Pale green, similar to 145A-B of the Yellow-Green Group.
Leaf glands:
*Size*.—Approximately 2 mm in height and less than 1 mm in width.
*Number*.—Generally 0-2 per leaf.
*Type*.—Reniform.
*Color*.—Varies from light brown to a dark reddish brown (163A, 164B-C, 165C-D, 172A-B and 173A-B of the Greyed-Orange Groups).
Leaf stipules:
*Size*.—Medium to long for the species.
*Length*.—Approximately 11 to 14 mm.
*Width*.—Less than 1 mm.
*Form*.—Lanceolate.
*Color*.—Medium to light green (139C-D of the Green Group) with reddish brown tips (176D and 177C-D of the Greyed-Orange Group) when young. The stipules are considered to be early deciduous.
*Ratio of wood (leaf) buds to flowering buds*.—1 to 2 flower buds per vegetative bud.

Flowers

Floral buds:
*General*.—The floral buds are considered to be medium to medium large in size, conic in form, and slightly appressed relative to the bearing shoot.
*Color*.—The bud scales are silver-brown, (approximately 197A-B of the Greyed-Green Group, N199B of the Grey-Brown Group and 200B of the Brown Group). The buds are considered hardy under typical conditions of the medium chill zone of Texas and the central San Joaquin Valley, Calif.
*Length*.—Approximately 5 to 6 mm.
*Width*.—Approximately 2.5 to 3 mm.
*Blooming type*.—Considered medium early in relation to other peach cultivars commonly growing in the medium chill zone of Texas. Date of full bloom was between February 28th and March 13th during the period between 2007 and 2012. Mean bloom date was March 7th which is about 2 days before 'June Gold' is in full bloom.
*Flower type*.—Non-showy.
*Flower size*.—Flower diameter at full bloom is approximately 24 to 29 mm. The length of the flower at the pink bud stage before opening ranges from 8 mm to 17 mm depending on its stage of development.
*Bloom quantity*.—Considered abundant.
*Flower bud frequency*.—Normally 1 to 2 per node.
Petal size:
*General*.—Considered small for the species.
*Width*.—Approximately 7 to 9 mm.
*Length*.—Approximately 14 to 16 mm.
*Petal form*.—Broadly ovate.
*Petal count*.—Nearly always 5.
*Petal color*.—Light pink center (Red-Purple Group 62D and 65A-B) with medium pink edges (Red-Purple Group 62B-C and 63C-D).
Petal claw:
*Form*.—The claw is of average size when compared to other varieties.
*Length*.—Approximately 1 to 1.5 mm.
*Width*.—Approximately 1 mm.
*Petal margins*.—Generally considered undulate.
*Petal apex*.—Generally — The petal apices appear slightly domed.
Flower pedicel:
*Length*.—Considered short, and having an average length of approximately 2 to 4 mm.
*Thickness*.—Considered average, approximately 1.5 mm.
*Color*.—A light green (Yellow-Green Group 144D and N144C-D).
Floral nectaries:
*Color*.—Considered quite variable in color from bright orange to orange to white (Orange Group 24A, 25A-B, N25A-B, 28A-B and White Group 155A-D).
Hypanthium:
*Surface texture*.—Generally glabrous.
*Color*.—Maroon with a green background (Red-Purple Group 60A, Yellow-Green Group 144D, N144C-D, 145A-B, Greyed-Purple Group 183A-C, 184A-B and 185A).
Sepals:
*Surface texture*.—The surface has a short, fine, and wooly texture.
*Size*.—Average, and ovate in form. The sepals vary in length from approximately 5.0 to 6.3 mm and in width from approximately 4.1 to 4.7 mm during the pink bud stage of development.
*Color*.—Maroon with a green background (Red-Purple Group 60A, Yellow-Green Group 144D, N144C-D, 145A-B, Greyed-Purple Group 183A-C, 184A-B and 185A).
Anthers:
*General*.—Average in size for the species. The length is approximately 1 mm and the width is approximately 0.5 mm.
*Color*.—Golden yellow (Yellow Orange Group 14A-B, 15A and 17A-B).
*Pollen production*.—Pollen is abundant, and is a yellow color (approximately Yellow Groups 5A-B and 12A-13B).
Filaments:
*Size*.—Variable in length, approximately 12 to 16 mm, with the filaments slightly shorter or equal to the pistil at the pink bud stage of development before the flower opens. The position of the stamen with respect to the pistil varies with the stage of flower development. At the beginning of the pink bud flower stage, the pistil protrudes from the flower with the stamens still enclosed in the flower. As the flower develops, the filaments continue extending such that as the flower opens, the stamens are at the same level or higher than the pistil.
*Color*.—White (approximately White Group 155A-D) and developing a very light pink (Red-Purple Group 65C-D) — with advanced maturity.

Pistil:

*General*.—Average in size, but slightly longer than or equal to the general anther height at the late pink bud stage of flower development.

*Length*.—Approximately 10 to 17 mm, including the ovary.

*Color*.—Considered a light green when young (approximately Yellow-Green Group 151A).

*Pubescence*.—Absent. The pistil, including the ovary, is not pubescent.

Fruit

Maturity when described: The present variety of fruit is described, as it would be found in its firm ripe condition at full commercial maturity. Under the ecological conditions prevailing in the medium chill zone of Texas 'Smooth Texan Three' ripens in late May to early June, a few days after 'June Gold'.

Size: General—Medium to medium large for the season and considered uniform.

Average cheek diameter: Approximately 60 to 62 mm.

Average suture diameter: Approximately 56 to 59 mm.

Average axial diameter: Approximately 58 to 63 mm.

Fruit form: Generally considered oblate with unequal halves. Occasionally the fruit exhibits less symmetry when comparing the suture height with the line opposite the suture. The fruit is generally uniform in symmetry when viewed from the apical aspect.

Fruit suture: Generally, the suture appears as a thin line that extends from the base to the apex, and appears deeper at the apex, forming a shallow basin at the apical point. No apparent callusing or stitching exists along the suture line.

Color: Generally, the colors of the blush (Orange-Red Group N34A, Red Groups 45A-B and 53A and Red-Purple Group 59A-B) and ground colors (Yellow Groups 11A and 13C and Yellow-Orange Group 14C).

Ventral surface: Form—Considered uniform.

Stem cavity:

*Size*.—Considered shallow for the species.

*Width*.—Approximately 8 to 9 mm.

*Length*.—Approximately 8 to 13 mm.

*Depth*.—Approximately 8 to 10 mm.

*Fruit base*.—Flat.

*Fruit apex*.—Flat and round.

Fruit stem:

*Length*.—10 to 16 mm.

*Thickness*.—Approximately 3 mm.

Fruit skin: Generally considered medium or average in thickness.

*Surface texture*.—Smooth.

*Skin acidity*.—Considered neutral.

*Tenacious to flesh*.—Yes at commercial maturity.

*Tendency to crack*.—Not observed.

*Skin color*.—Generally — Variable, with approximately a medium (60%) to a very large (90%) percentage of the fruit surface covered with an attractive blush as described in Blush Color.

*Pubescence*.—Absent. The glabrous fruit has medium to strong glossiness.

*Blush color*.—The blush ranges from a medium to dark red (Orange-Red Group N34A, Red Groups 45A-B and 53A and Red-Purple Group 59A-B) with many degrees of shading and blending between these colorations.

*Skin ground color*.—Medium yellow (Yellow Groups 11A and 13C and Yellow-Orange Group 14C).

*Flesh color*.—Generally considered medium to light yellow and ivory (Yellow Groups 10C-D and 11C-D and Yellow-White Group 158B-C).

*Flesh fibers*.—Present, numerous and lightly colored. These fibers are present throughout the flesh.

*Stone cavity color*.—Generally considered medium to light yellow and ivory (Yellow Groups 10C-D and 11C-D and Yellow-White Group 158B-C).

*Flesh texture*.—Generally, the flesh is considered firm and fine at commercial maturity.

*Ripening*.—Generally the fruit of the present variety ripens evenly.

*Flavor*.—Considered very sweet with sub-acid flavor.

*Aroma*.—Pleasant and reasonably abundant.

*Eating*.—Generally considered very good to excellent, particularly for an early mid season ripening variety.

Stone

Attachment: Clingstone (strongly adherent) at commercial maturity.

Stone size: Generally considered medium to medium-large relative to the ratio of stone to fruit size.

*Length*.—Approximately 31 to 36 mm.

*Width*.—Approximately 23 to 27 mm.

*Thickness*.—Approximately 18 to 21 mm.

*Fibers*.—Generally several fibers are attached along the surface of the stone.

*Stone form*.—Considered variable, from elliptical to ovate.

*Stone base angle*.—The stone is medium to wide.

*Apex shape*.—Variable, from medium to wide.

*Stone shape*.—Considered variable, ovoid to elongated.

Stone surface:

*Surface texture*.—Consists of single pits, rosettes of pits, chains of pits and pit grooves.

*Ridges*.—A few ridges are present basally.

*Ventral edge*.—Medium.

*Dorsal edge*.—Shape — Grooved and having moderately rough edges.

*Stone color*.—The color of the dry stone is light brown (although difficult to match, similar colors include 164C-D, 165C-D and 166C of the Greyed-Orange Group and N199C-D of the Grey-Brown Group). The color of the inside surface of the endocarp is primarily Greyed-Orange 164C-D and 165C-D.

*Tendency to split*.—Splitting is relatively uncommon.

*Kernel*.—The kernel fills the endocarp at harvest and measures approximately 4-5 mm in thickness, 10-11 mm in width, and 15-17 mm in length. When dried the shriveled kernels measure approximately 1 mm in thickness, 7-10 mm in width, and 14-15 mm in length. The colors of the shriveled kernels are primarily 164C-D and 165C-D of the Greyed-Orange Group.

Use: The subject variety, 'SMOOTH TEXAN THREE', is considered to be a nectarine tree of early mid-season maturity, which produces fruit which are firm, attractively colored, and which are useful for both local and regional markets.

Keeping quality: Good to very good.

Resistance to insects and disease: In plots in Texas, bacterial leaf spot [*Xanthamonas campestris* pv. *pruni* (Smith) Dye] was observed on both fruit and leaves.

Shipping quality: Average.

Although the new variety of nectarine tree possesses the described characteristics when grown under the ecological conditions prevailing near College Station (Brazos county) and Fairfield (Freestone county), Tex. it will be understood that variations of the usual magnitude and characteristics incident to the changes in growing conditions, fertilization, pruning, and pest control are to be expected.

REFERENCES

Anderson, F. W. 1972. Red Diamond nectarine tree. U.S. Plant Pat. No. 3,165. May 9, 1972.

Anon. 2001. R.H.S. Colour Chart. The Royal Hort. Soc., London.

Brooks, R. M. 1958. Double Delight, Earligold, and June Gold peaches. Fruit Var. J. 3:22.

Bradford, L. G. and N. G. Bradford. 1994. Nectarine tree (Diamond Ray). U.S. Plant Pat. No. 8,948, Oct. 18, 1994.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

We claim:

1. A new and distinct *Prunus persica* tree, substantially as illustrated and described herein.

* * * * *